United States Patent [19]

Bouse et al.

[11] Patent Number: 5,084,395
[45] Date of Patent: Jan. 28, 1992

[54] REDUCIBLE INDICATOR COMPOSITIONS CONTAINING PYROGALLOL DERIVATIVES

[75] Inventors: Lee Bouse, Indianapolis; Michael Phillips, Pittsboro, both of Ind.

[73] Assignee: Boehringer Mannheim GmbH, Mannheim, Fed. Rep. of Germany

[21] Appl. No.: 554,733

[22] Filed: Jul. 18, 1990

Related U.S. Application Data

[62] Division of Ser. No. 198,765, May 25, 1988, Pat. No. 4,971,918.

[51] Int. Cl.⁵ ............................................. G01N 21/75
[52] U.S. Cl. ..................................... 436/166; 436/63; 436/66; 436/164; 422/55; 422/56
[58] Field of Search ................ 422/55, 56; 436/13–16, 436/164, 63, 66, 166

[56] References Cited

U.S. PATENT DOCUMENTS

| | | | |
|---|---|---|---|
| 4,418,037 | 11/1983 | Katsuyama et al. | 422/56 |
| 4,447,542 | 5/1984 | Gantzer | 422/56 |
| 4,643,588 | 2/1987 | Postle et al. | 422/57 |

*Primary Examiner*—Robert J. Warden
*Assistant Examiner*—Lyle Alfandary-Alexander
*Attorney, Agent, or Firm*—Felfe & Lynch

[57] ABSTRACT

The invention relates to a composition useful in determining an analyte in a sample. The composition contains an indicator system which forms a detectable signal in the presence of said analyte, and which is not a coupling system, as well as a pyrogallol derivative. The pyrogallol derivative causes uniform formation of detectable signal. Also described are kits useful in determining an analyte, apparatus which incorporate the composition, and a method for determining an analyte using the composition.

14 Claims, 12 Drawing Sheets

3,3',5,5' - TETRAMETHYLBENZIDINE INDICATOR SUBSTITUTED FOR O-TOLIDINE IN THE CHEMSTRIP bG III PAD

N-BUTYL GALLATE

ISOBUTYL GALLATE

FIG. 7. GALLIC ACID

METHYL GALLATE

PROPYL GALLATE

OCTYL GALLATE

LAURYL GALLATE

GALLATE DERIVATIVES

REDUCIBLE INDICATOR COMPOSITIONS CONTAINING PYROGALLOL DERIVATIVES

This is a divisional application of application Ser. No. 198,765, filed May 25, 1988 now U.S. Pat. No. 4,971,918.

FIELD OF THE INVENTION

This invention relates to compositions useful in determining an analyte in a sample, analytical devices incorporating these compositions, as well as methods for determining an analyte.

BACKGROUND AND PRIOR ART

The field of analytical and diagnostic chemistry has grown tremendously in recent years. The field relates to analysis of body fluids, such as blood, serum, urine and the like, food substances, such as milk, drinking water, and other fluid substances. Applications of the field include medical diagnosis, purity testing, forensic science, etc.

The apparatus employed in analytical chemistry of the type discussed herein is generally a device referred to at times as a test strip, a dip stick, or other terms which will be familiar to those skilled in the art. The device contains various substances incorporated therein, which react with a particular analyte, or substance to be determined, with formation of a determinable or detectable signal. Frequently, but not always, this is a color. Color formation, or change in color, permits one to give a "yes-no" answer to the question of whether a substance or analyte is present in a test sample. Degree of color formed, or the actual color, can be used as an indication of how much analyte is present.

In practice, the sample may be applied to the test device, or the device may itself be dipped in or otherwise contacted to the test sample.

One very common test which is presented as exemplary of the type of assay performable with test devices and dry chemistry is a determination of blood glucose level. This, of course, is important in many situations, such as monitoring of diabetic and hypoglycemic patients. A test strip is prepared which contains the enzymes glucose oxidase and a peroxidase, as well as the indicator 3,3',5,5'-tetramethylbenzidine, also referred to as "TMB". If glucose is present in the sample, it reacts with oxygen in the presence of glucose oxidase to form gluconic acid and hydrogen peroxide. In the presence of peroxidase the peroxide, in turn, reacts with the TMB. TMB, in unoxidized form, is colorless. When oxidized, it forms a color in the range of blue to purple. Thus, one can determine if glucose is present, and in what concentration, by observing formation of color. The system is analyte specific, because hydrogen peroxide is not a normal component of the sample, and only forms when the glucose specific enzyme glucose oxidase acts on its substrate.

The system described supra, is, of course, only one example of the various assays which can be performed using dry chemistry techniques. By modifying the analyte specific enzyme and indicator, one can, of course, determine different analytes, using the system outlined.

Many different types of indicators are available to the clinical chemist. A broad class of such indicators, or indicator systems, rely on the oxidative coupling of two different components to produce an indicator or dye. Exemplary of such systems is the so-called "Trinder reagent", as taught by Trinder, Ann. Clin. Biochem 6:24 (1969). This system is used to determine glucose, cholesterol, and uric acid in body fluids such as serum and plasma.

Trinder reagents involve the coupling of substituted or unsubstituted phenols with 4-aminoantipyrine (4-AAP), to form a red dye. This reaction:

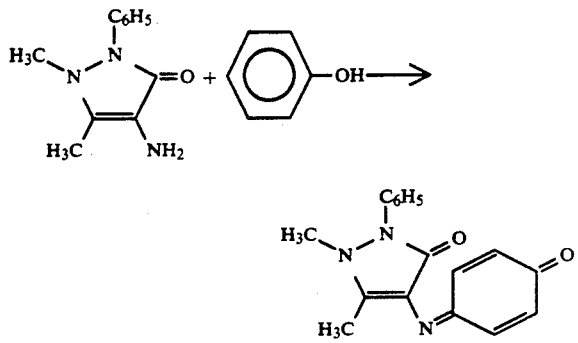

is described in Acquati, et al., U.S. Pat. No. 4,291,121, the disclosure of which is incorporated by reference herein. Acquati, et al., teach that various substituted phenols, can be used as the coupling compound for the indicator system.

Acquati, et al. also point to a problem in indicator systems, i.e., interference by components of the sample being tested. The interference in Acquati, et al., results in competition between the compound being determined (cholesterol, glucose, uric acid, etc.), and reducing agents for the indicator system and lower values for the analyte than actually exist.

Klose, et al., in U.S. Pat. No. 4,101,381 teach another type of indicator system: that of the indicator system which produces a charge carrying or "reducible" chromogen. This patent teaches that the compound 3-methyl-2-(sulfonyl)-benzothiazolone hydrazone (MBTHS), reacts in the presence of formaldehyde and an oxidizer to produce a reducible chromogen.

Other indicators such as 3,3',5,5' tetramethylbenzidine (TMB) and its derivatives form charge carrier complexes rather than "coupled oxides" in the manner of Trinder reagents. The charge carrier complexes also serve as indicators in that, when the molecules are not complexed they either carry no color or are a different color from that of the complex.

When these indicators are reduced, however, they do not produce a color. Hence, they are reducible chromogens. Examples, in addition to TMB and MBTH are o-dinisidine, guaicol, and o-tolidine.

This distinction between charge carriers and couplers has been described as well by Katsuyama, et al., U.S. Pat. No. 4,418,037, who describe the distinction as being between "reducible chromogens" and "combination of a hydrogen donor (developing agent) and a coupler". Katsuyama, et al. teach that there is a problem in indicator systems in that enzymes used therein frequently become inactivated, slowing down the reaction producing the signal. In order to avoid this, they propose the addition of pyrogallol derivatives to systems which in their oxidized state "couple with a coupler such as naphthol, a phenol, a pyrazoline or N,N-disubstituted anilines" (column 6, lines 54-60). All of Katsuyama, et al.'s examples require coupling compounds.

Katsuyama teaches that the pyrogallol derivative acts as a "preservative" for the enzyme in the test system. Expressed another way, this patent teaches that in systems using coupling indicators, the shelf-life of the strip is increased. The indicator reaction takes places in the same way it would were the pyrogallol derivative not present.

It has now been found, however, that pyrogallol derivatives, when used in connection with reducible chromogens act in a manner not expected from Katsuyama. It has been found that indicator systems using reducible or charge carrying chromogens function differently "after" addition of pyrogallol than they do before. This is significant because the addition of pyrogallol derivatives to the aforementioned indicator system extends the range of such systems. This will be explained in more detail infra.

Hence it is an object of this invention to provide a composition useful in determining an analyte in a sample, which contains an indicator system characterized by a reducible charge carrier forming chromogen, and a pyrogallol derivative.

It is a further object of the invention to provide kits which can be used to detect analytes in samples, which kits include the above referenced components.

It is a further object of the invention to provide analytical apparatus which can be used to determine analytes, which also use the above identified compositions and kits.

It is still another object of the invention to provide a method for the determination of an analyte in a sample using the above compositions, kits, and analytical apparatus.

How these and other objects of the invention are achieved will become apparent after review of the disclosure which follows.

DETAILED DESCRIPTION OF PREFERRED EMBODIMENTS

The compositions of the invention comprise an indicator system including a reducible or charge carrier complex forming chromogen, and a pyrogallol derivative. By reference to the earlier discussion, it will be understood that an indicator system which does not require a coupling compound is one where a detectable signal is generated without the formation of a coupled moiety.

Of particular interest, and the preferred indicator system, is 3,3',5,5' tetramethylbenzidine ("TMB") hereafter, and 3-amino-9-(gamma aminopropyl) carbazol and its salts, such as the dihydrochloride salt. TMB is an indicator that does not couple to another compound in order to form its signal, which is a color ranging over the visible spectrum from blue, red, or purple, depending upon the charge complex formed.

TMB is typically used in detection systems to determine glucose. In these systems, a pair of reactions take place. The sample containing the glucose is contacted to a system which contains the enzyme glucose oxidase (GOD), which, in the presence of oxygen, oxidizes glucose to gamma-D-gluconolactone and hydrogen peroxide. The hydrogen peroxide reacts with unoxidized TMB, usually in the presence of peroxidase (POD), to form a charge transfer complex of TMB, which carries a color. For glucose determination, this color is blue. Unoxidized TMB is colorless. Thus, the presence and/or intensity of blue color is an indication of the amount of glucose in a given sample.

The reaction discussed supra can be shown as follows:

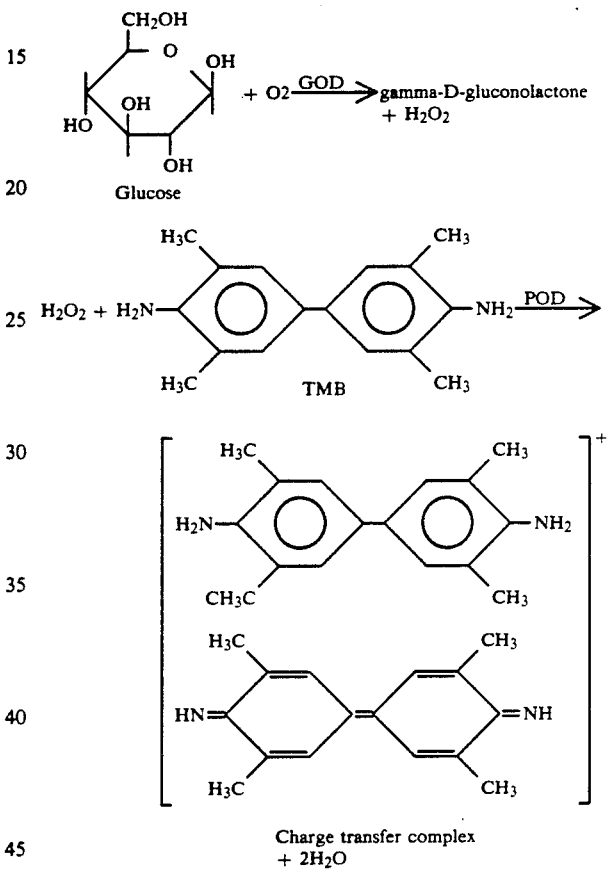

Charge transfer complex + 2H$_2$O

While TMB is depicted supra, and the examples which follow use this indicator, it will be understood that there are many indicator systems which operate via the formation of charge transfer complexes and means other than coupling. Generally, benzyl derived indicators do not couple: examples of these include o-tolidine, MBTH, MBTHS, and their derivatives, as well as derivatives of TMB. It is to be understood hereafter that TMB exemplifies this group of indicators, but it is not the only indicator which is expected to operate in the described invention.

TMB will work in the described system alone. While the system can be observed visually, and presence and/or concentration of glucose determined in this fashion, the preferred mode of determination is by means of a reflectance photometer, the operation of which is described infra.

The examples which follow do use TMB together with the compound 3-amino-9(-gamma aminopropyl)-carbazol, which will be referred to by its trade name "APAC" hereafter.

Figure 1:
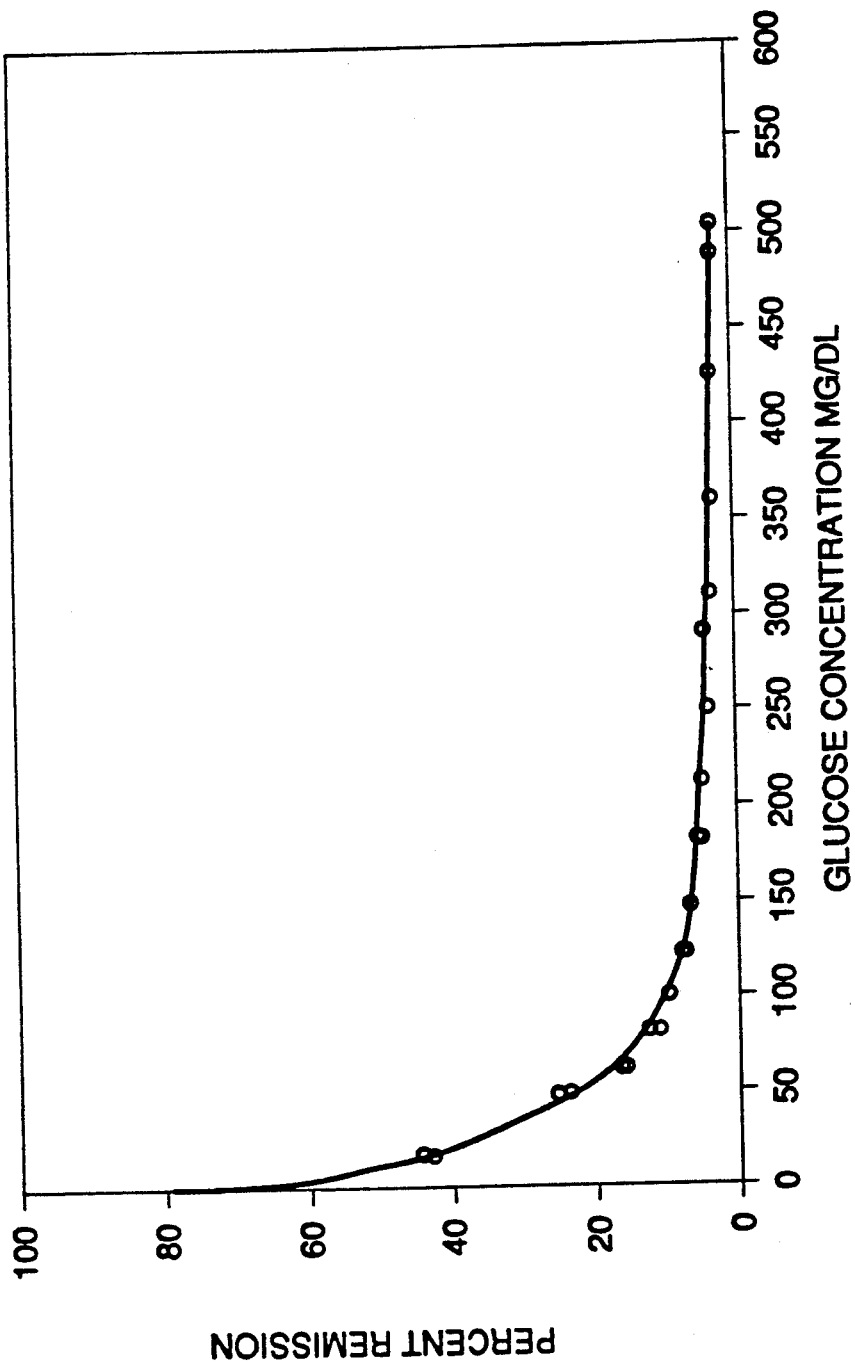
FIG. 1 is a graph of percent remission plotted against concentration of an analyte (glucose), without the use of a pyrogallol derivative as an inhibitor.
Figure 2:
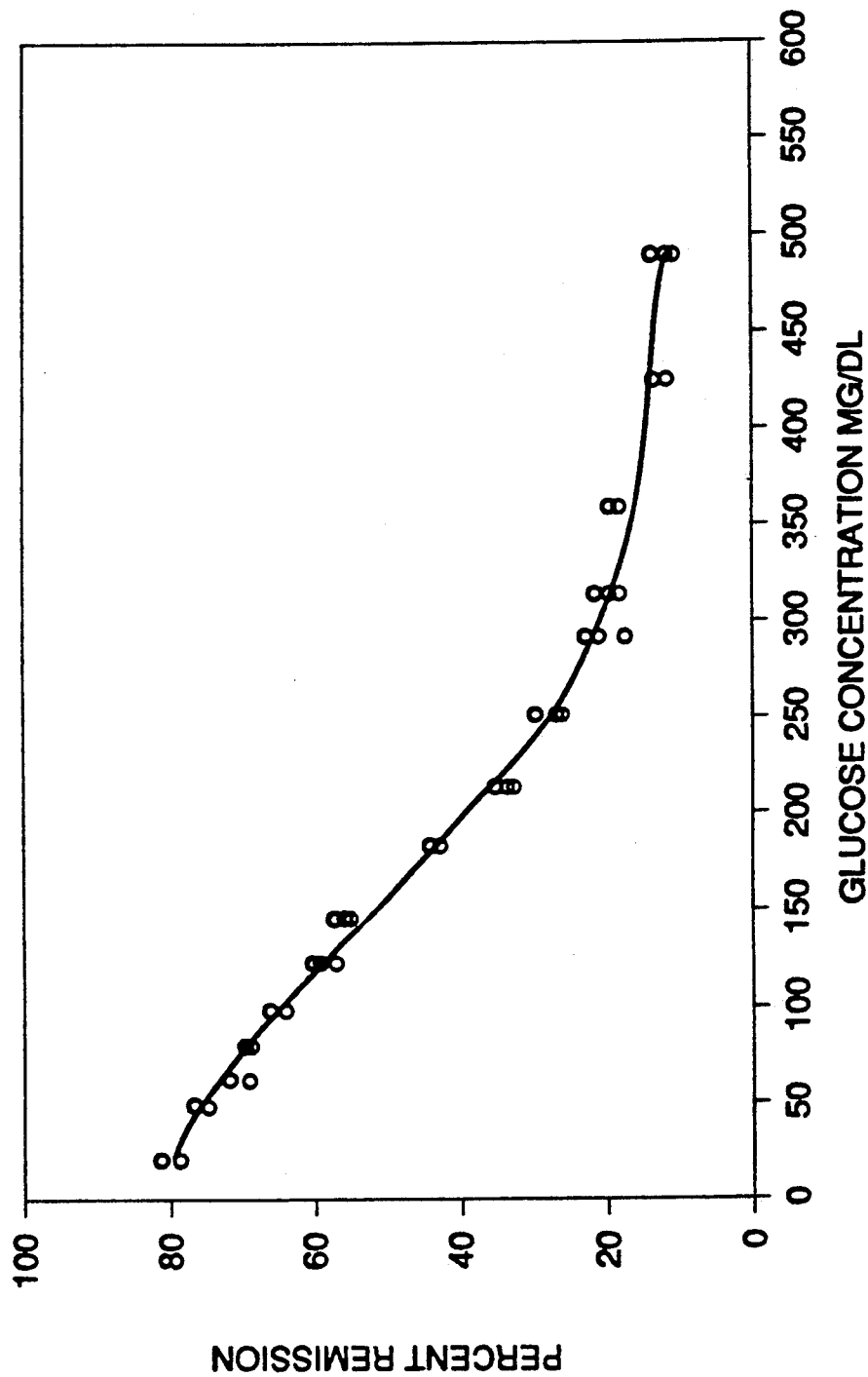
FIGS. 2-11 show similar graphs, using various gallate derivatives with the indicator system.
Figure 3:
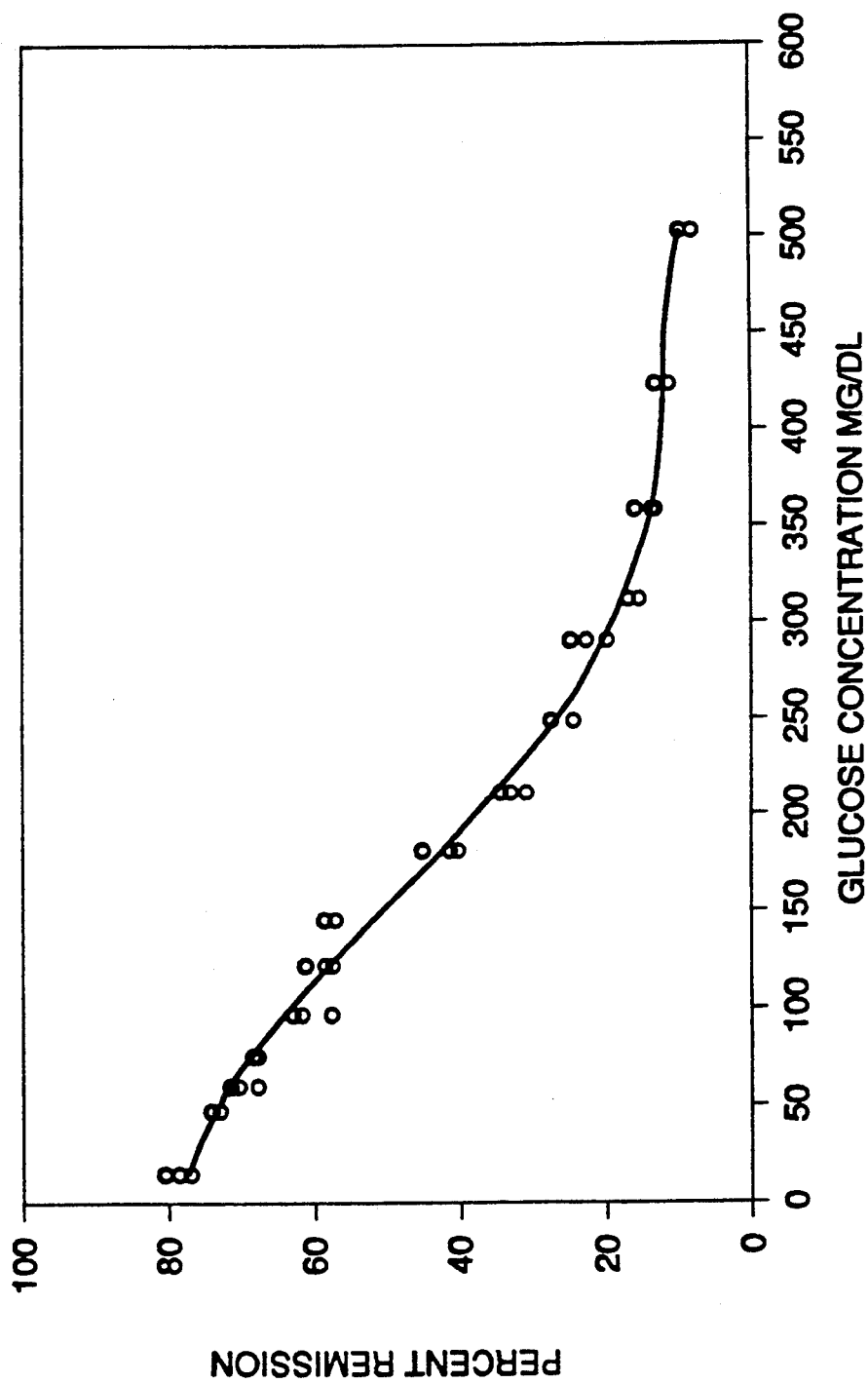
Figure 4:
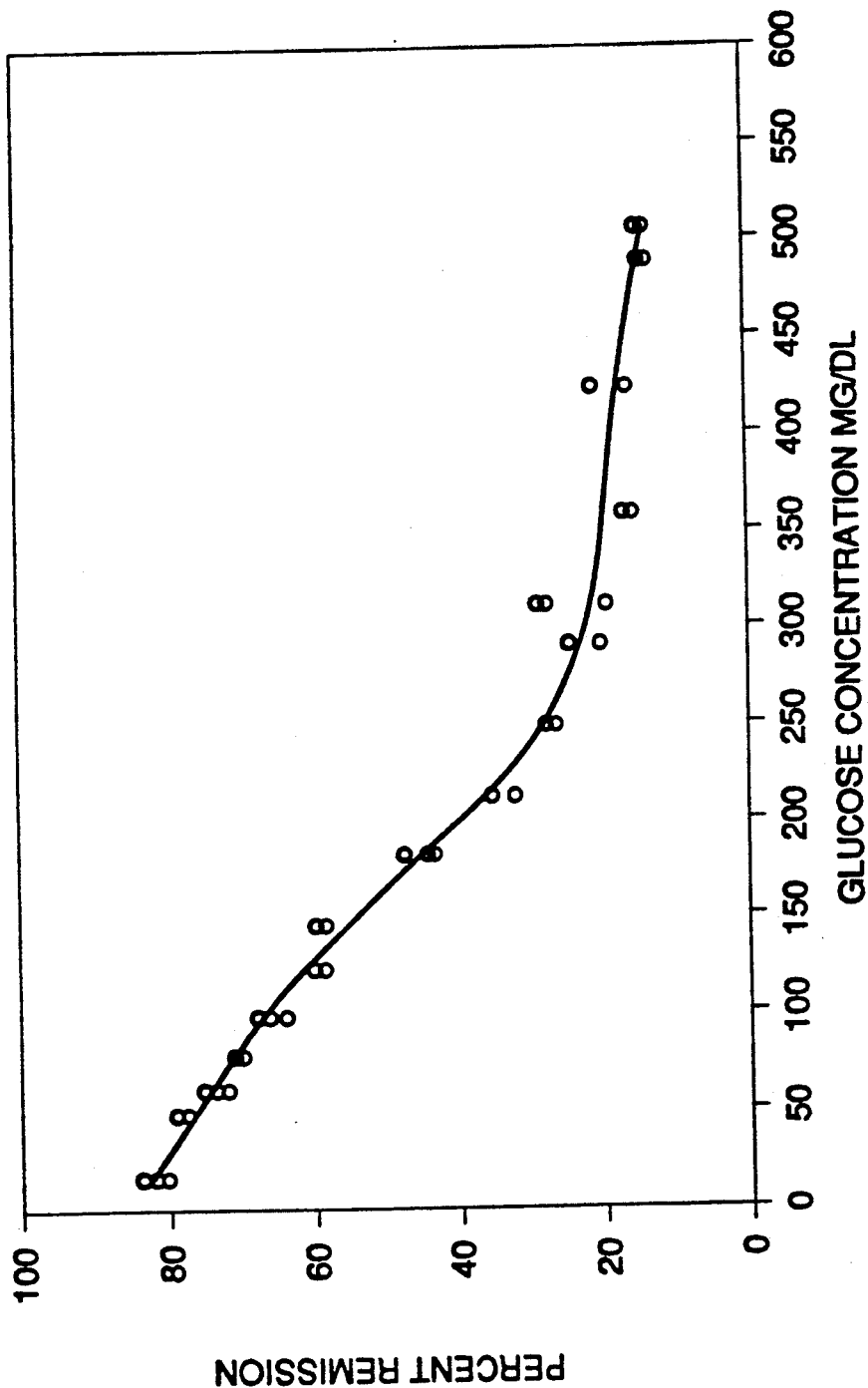
Figure 5:
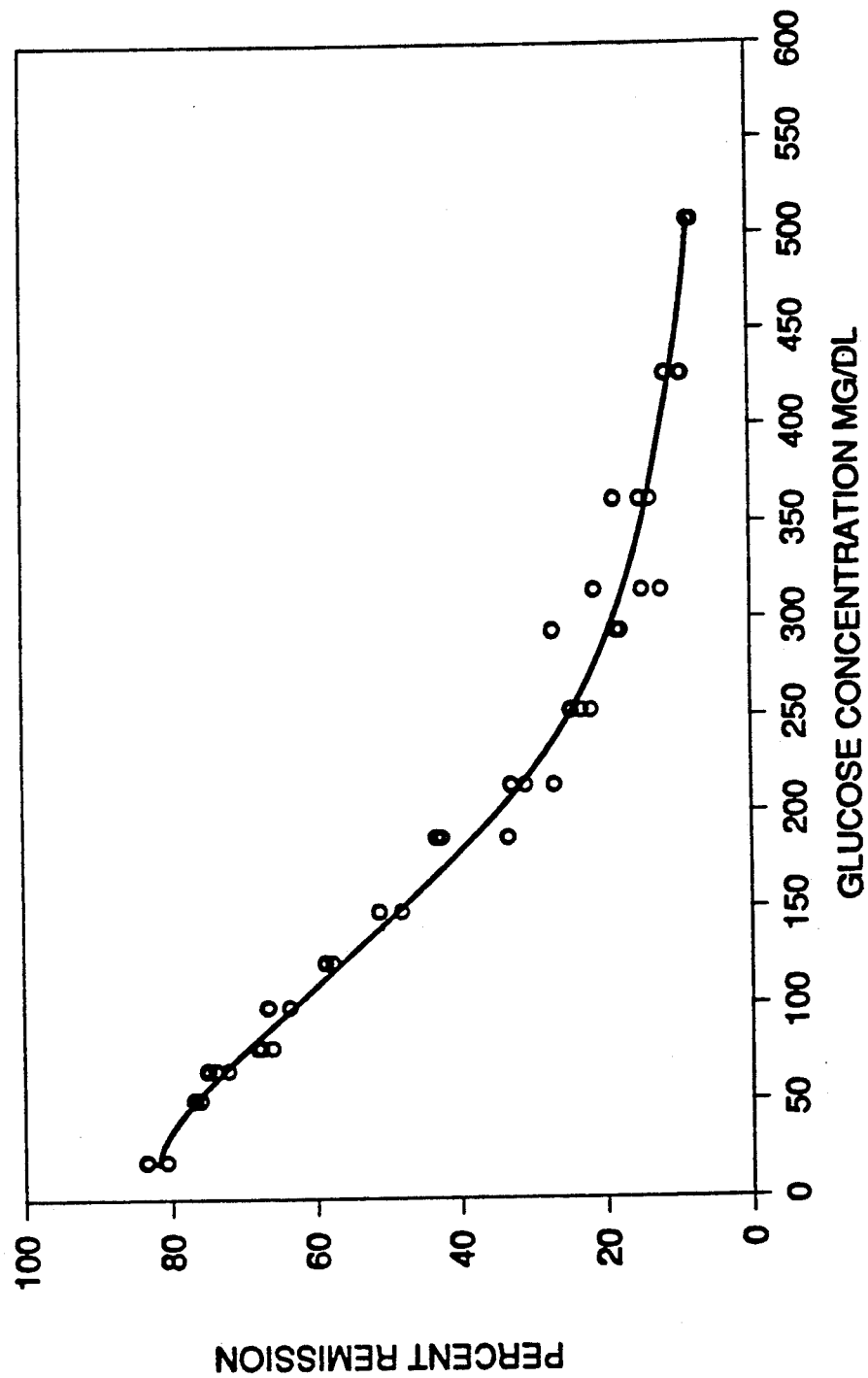
Figure 6:
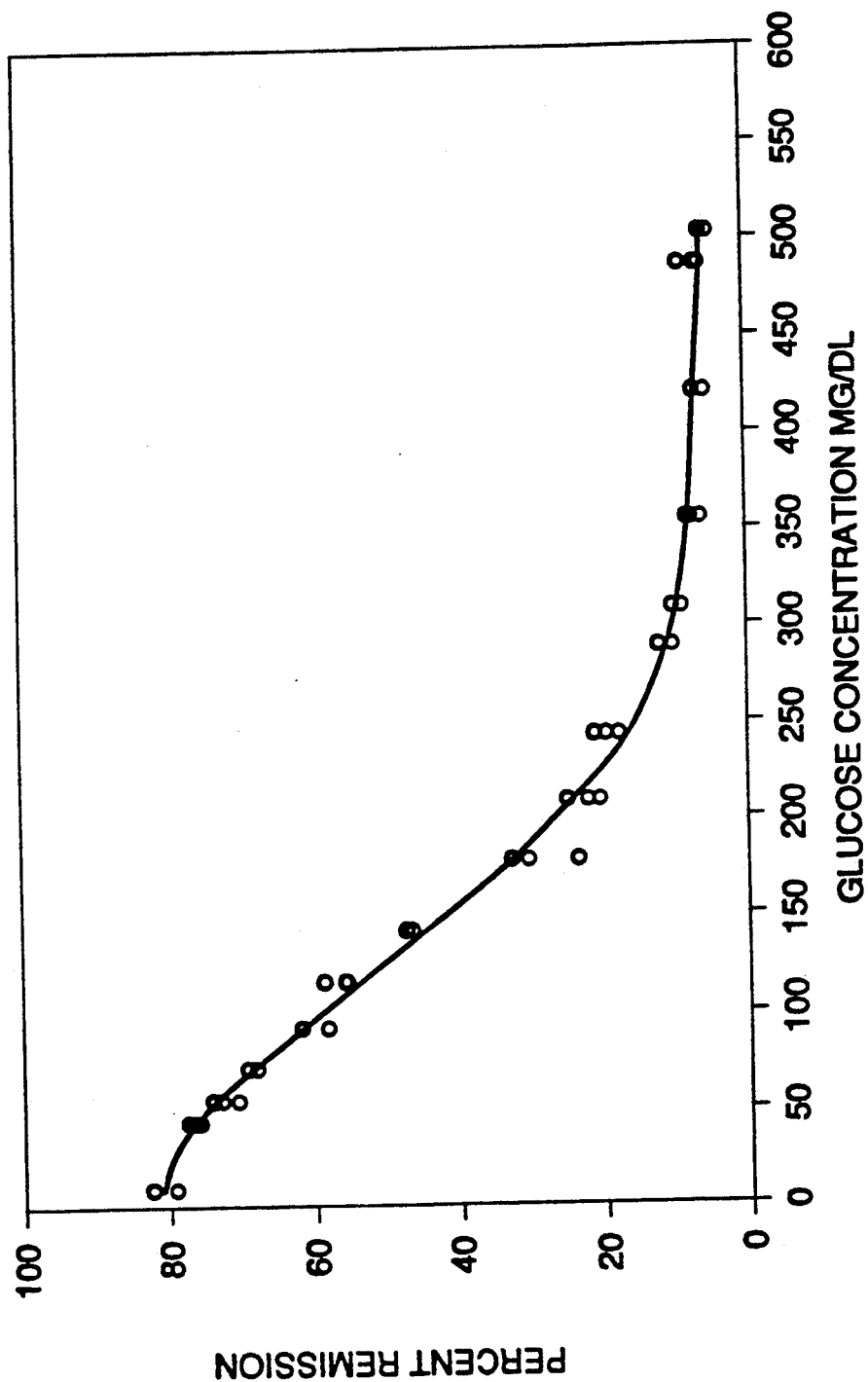

The problem with using TMB, or other similar indicators is shown in FIG. 1. FIG. 1 shows the "percent remission" obtained when TMB is used in the system described supra, in measuring glucose concentration. "Percent remission" refers to how much light is reflected from a test strip or other device used to measure a substance. A high remission value means that little color is formed, and, similarly, a low value indicates more intense color.

Referring to FIG. 1, it will be seen that a smooth curve is produced for TMB up to a concentration of about 100 mg/dl. At that point, however, the graph flattens, and the remission values are almost identical for all values from 100 mg/dl to 500 mg/dl. A value of 100 mg/dl is within the normal range of glucose in blood, but a value of 140 mg/dl or greater, after fasting, is an indication of *diabetes mellitus*. Reference to the graph in FIG. 1 will show that diagnosing for diabetes using TMB alone is contraindicated.

It has now been found, however, that incorporating a pyrogallol derivative in the indicator system "smooths out the curve", and extends the range of values over which diagnosis can be made.

Figure 12:
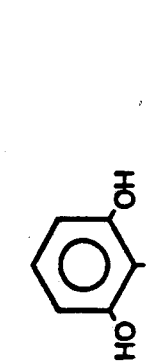
FIG. 12 shows the preferred gallate derivatives of the invention.

The pyrogallol derivatives used in this invention are represented by the formula:

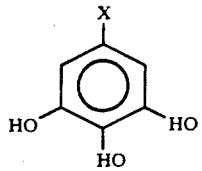

where X is hydrogen or O=COY, Y is hydrogen or $(CH_2)_4CHBD$, A is a whole number from 0 to 17, and B and D are the same and are either hydrogen or methyl. Of particular interest are compounds where X is hydrogen (pyrogallol); X is O=COY and Y is hydrogen (gallic acid); A is zero and B and C are hydrogen (methyl gallate); A is 2 and B and C are hydrogen (propyl gallate); A is 3, 7, 11, 15 or 17 and B and C are hydrogen (gallic acid N-butyl ester; octyl gallate; lauryl gallate; gallic acid cetyl ester; gallic acid steryl ester), and compounds where A is 1 or 2 and B and C are methyl (gallic acid isobutyl ester and gallic acid isoamyl ester). For convenience, these eleven preferred compounds are depicted in FIG. 12.

The following examples provide more details on the operation of the invention but are not to be viewed as limitative of any aspect thereof.

EXAMPLE 1

In this experiment, a test strip impregnated with 3,3',5,5'-tetramethylbenzidine and "APAC" only was used to determine the concentration of glucose in samples containing known amounts of glucose. The test strips impregnated with the reagents also contained glucose oxidase and peroxidase, so as to increase the speed of the reactions leading to formation of the colored signal produced by the TMB.

Samples of glucose with the given concentrations were applied to a test strip as described, and after 120 seconds were read in a reflectance photometer which had been corrected to compensate for interference caused by the surroundings.

In a reflectance photometer, one measures the difference between the intensity of light reflected from a nonabsorbing material (white) and the light which is reflected from the sample.

In this and the following experiments, the percent of reflection is graphed against glucose concentration.

FIG. 1 depicts the results of these experiments, and the problem with the system will be seen immediately. It is to be noted that at a glucose concentration of 0, the % reflectance is given as 70%.

In the normal range of glucose concentrations (i.e., from 70 to 110 mg/dl), there is some slope in the curve, and it is enough to distinguish a "low normal" sample (70 mg/dl) from a "high normal" (110 mg/dl). Compare this, however, to values at 140 mg/dl, which is generally considered to be the lower level range for *diabetes mellitus*. The curve from 110 to 140 mg/dl is almost linear, making it nearly impossible to diagnose a diabetic condition. The same flattening is evident for all of the values of to 500 mg/dL. It is impossible to distinguish the values.

EXAMPLES 2-6

In the following examples, assays for glucose were run, this time using APAC (described supra) with the TMB, and, in each case, a pyrogallol derivative (isoamyl ester 20 mgs, N-butyl ester 20 mgs, isobutyl ester 20 mgs, stearyl ester 40 mgs, and cetyl ester 40 mgs).

The test strips were prepared from the following composition, which was coated on to a polystyrene film and dried to a final thickness of 150 um:

| Composition of Solution for Test Strips | |
|---|---|
| Propiofan 70-D | 73 g |
| Sodium Nonyl Sulfate | 1.6 g |
| Sodium Alginate | 1.5 g |
| APAC | .13 g |
| TMB | 1.4 g |
| $KH_2PO_4$ | 5.0 g |
| $Na_2HPO_4$ | 0.7 g |
| GOD | .20 g |
| POD | .25 g |
| Pyrogallol Derivatives | as above |
| Acetone | 5 mL |
| $H_2O$ | 115 mL |

The tests were run in the fashion described in Example 1, and the results are depicted graphically in FIGS. 2-6, which also show the color development of the indicator system. Two runs were performed for each concentration.

It will be apparent from these graphs that a clean distinction can be drawn between different values of the glucose concentration. "Linearization" does not begin to occur until a concentration of about 300 mg/dL, as compared to the system which did not use a pyrogallol derivative and which linearized at only 100 mg/dL. Smoother, more even curves have been obtained, In the case of the cetyl and stearyl esters, the initial values approach 90%, and the following curves are very smooth, leading to a preference for these compounds in the indicator compositions.

EXAMPLE 7

Figure 7:
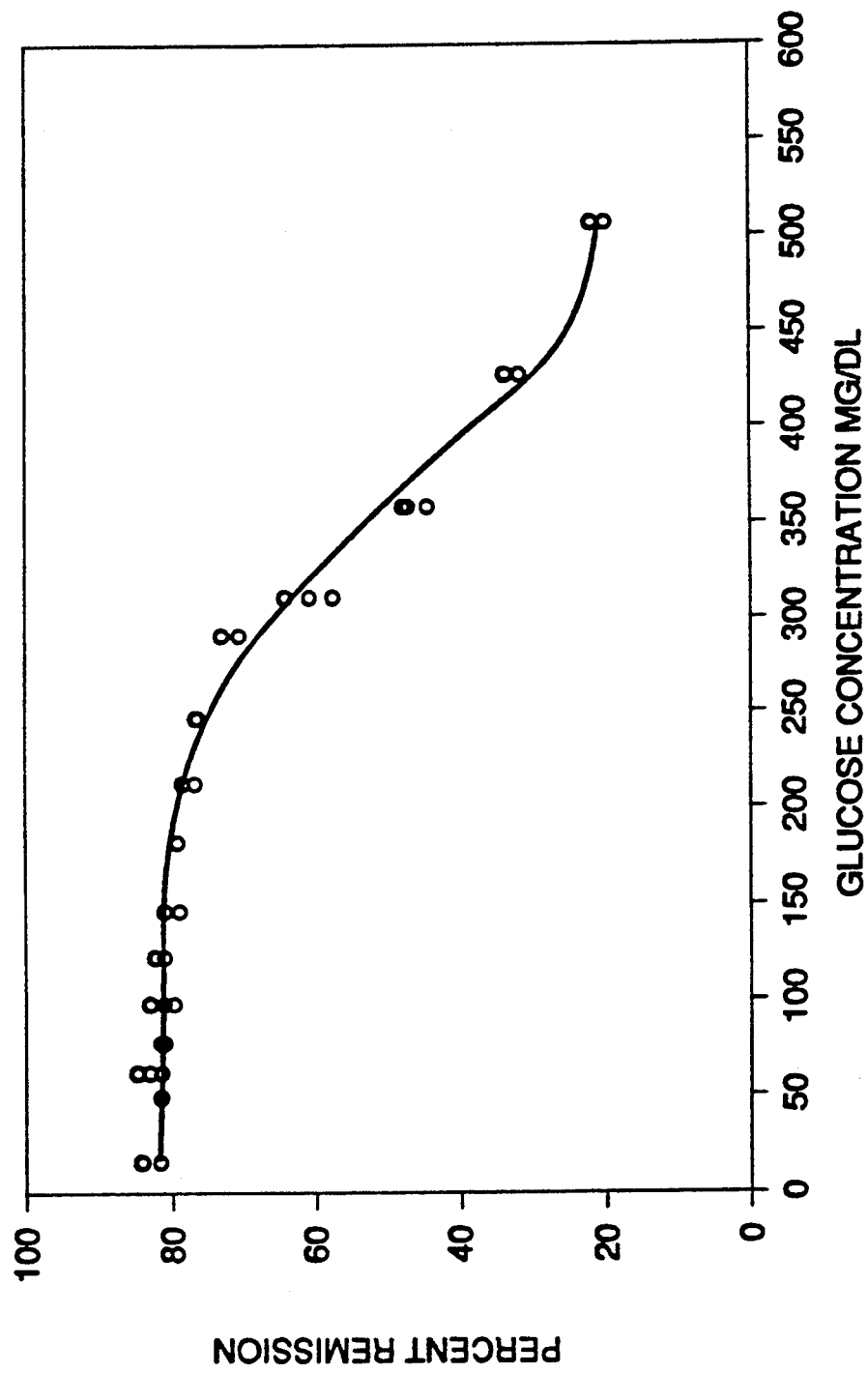

An experiment similar to those performed in examples 2-6 was carried out the only difference being that the gallate derivative used was gallic acid, at 50 mg. The curve of values obtained is shown in FIG. 7.

What is interesting about this experiment is that gallic acid permits one to make distinctions at very high levels, at the point where the gallate derivatives used in Examples 2-6 begin to "linearize". This suggests that one could use a two test strip system where glucose levels which are very high are indicated. In other words, one tests first with one of the gallate derivatives of Examples 2-6, and, if a very high value (e.g., 300 mg/dl or more) is indicated, a second test could be performed using gallic acid.

EXAMPLES 8 AND 9

Figure 8:
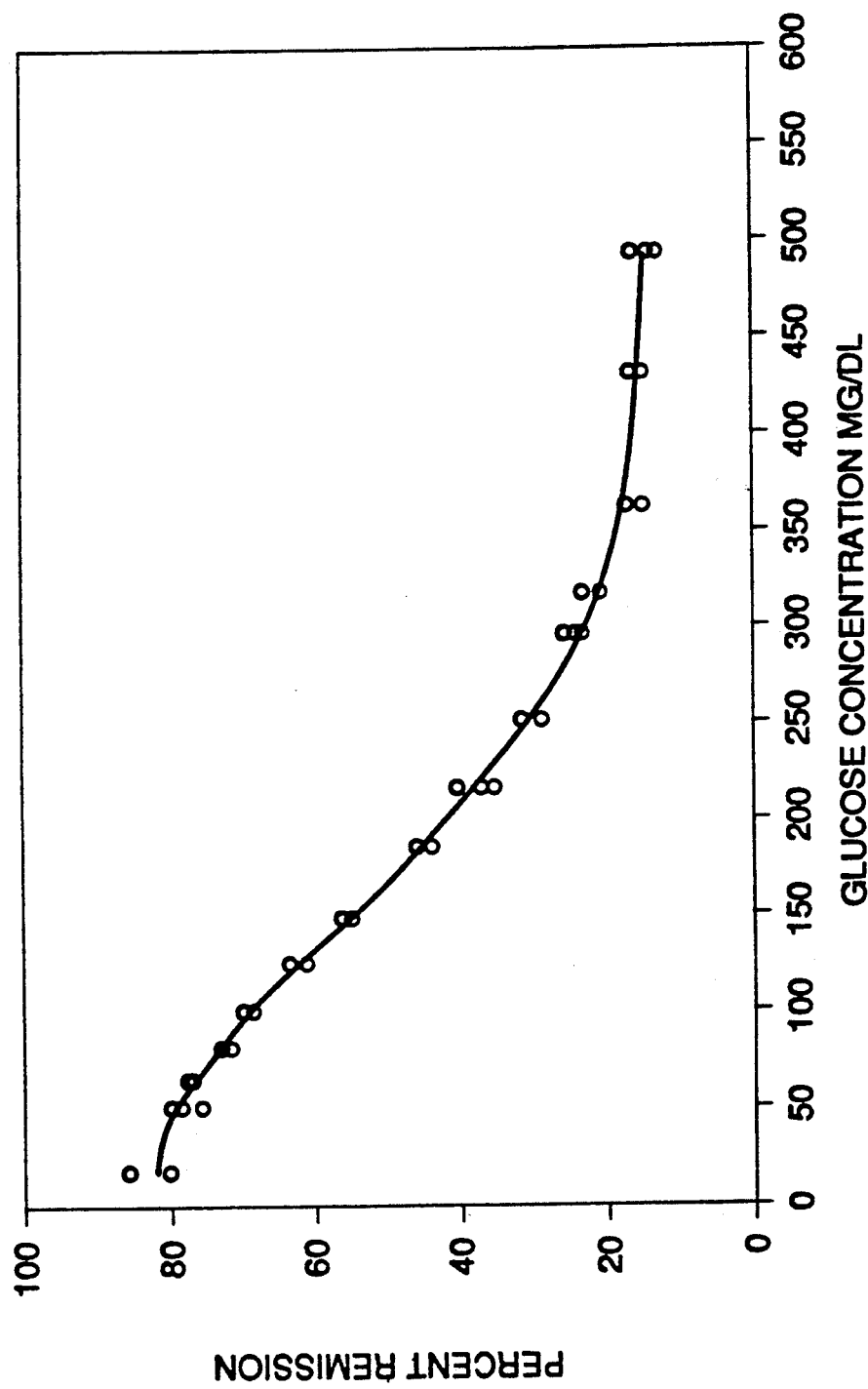
Figure 9:
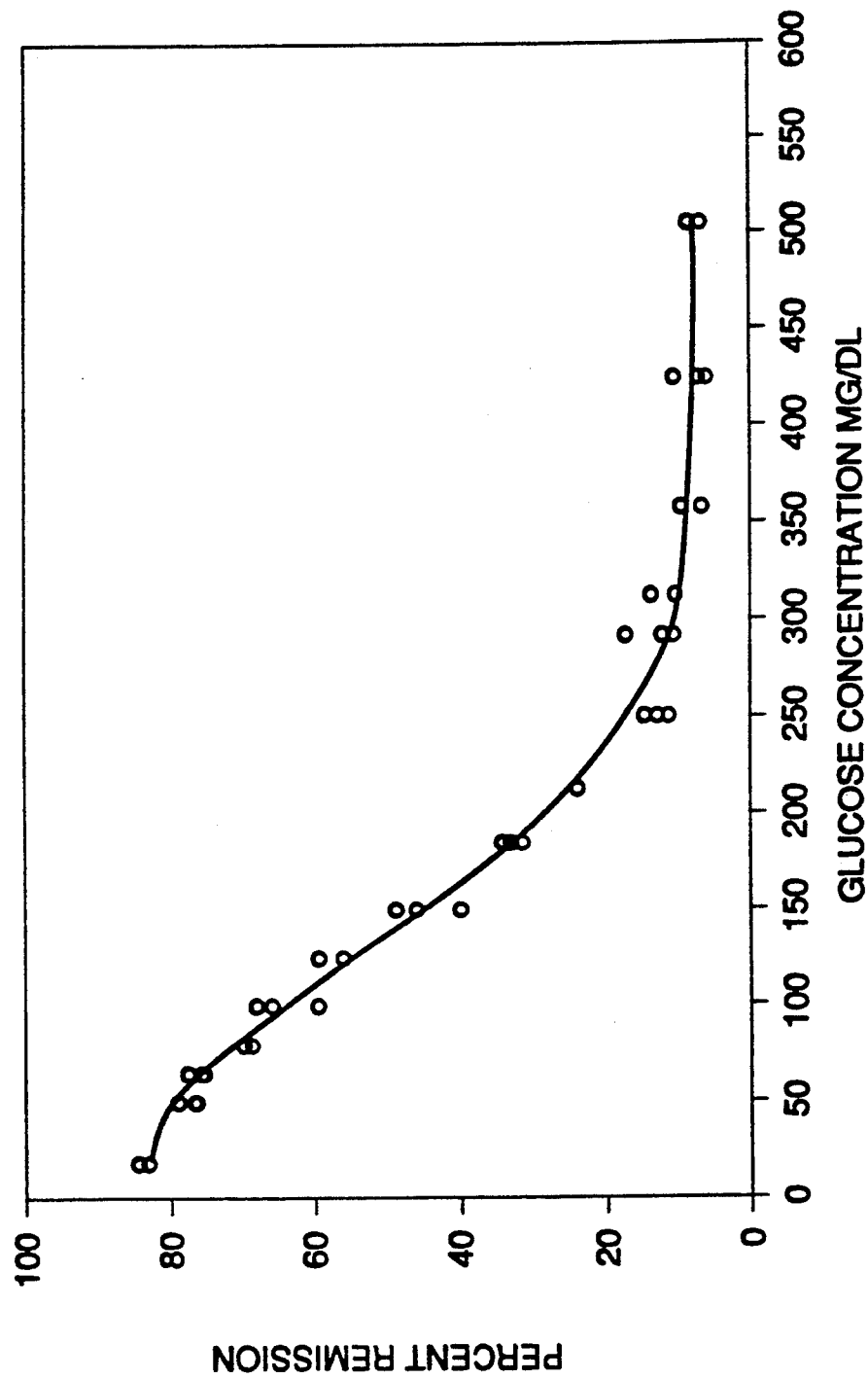

A set of experiments were performed, also in a fashion similar to those described supra, using the methyl and propyl gallate derivatives. Two different amounts of the derivative were used (30 mg and 40 mg, respectively), and the results shown in FIGS. 8 and 9.

It will again be seen that the gallate derivative caused the desired uniformity in color formation, with delineation of different concentrations evident. Note that the use of propyl gallate produced an almost ideal results—i.e., a line with uniform downward slope

EXAMPLES 10 AND 11

Additional examples were performed using the octyl and lauryl derivatives (50 mgs in each case). The composition is otherwise identical to that described supra.

Figure 10:
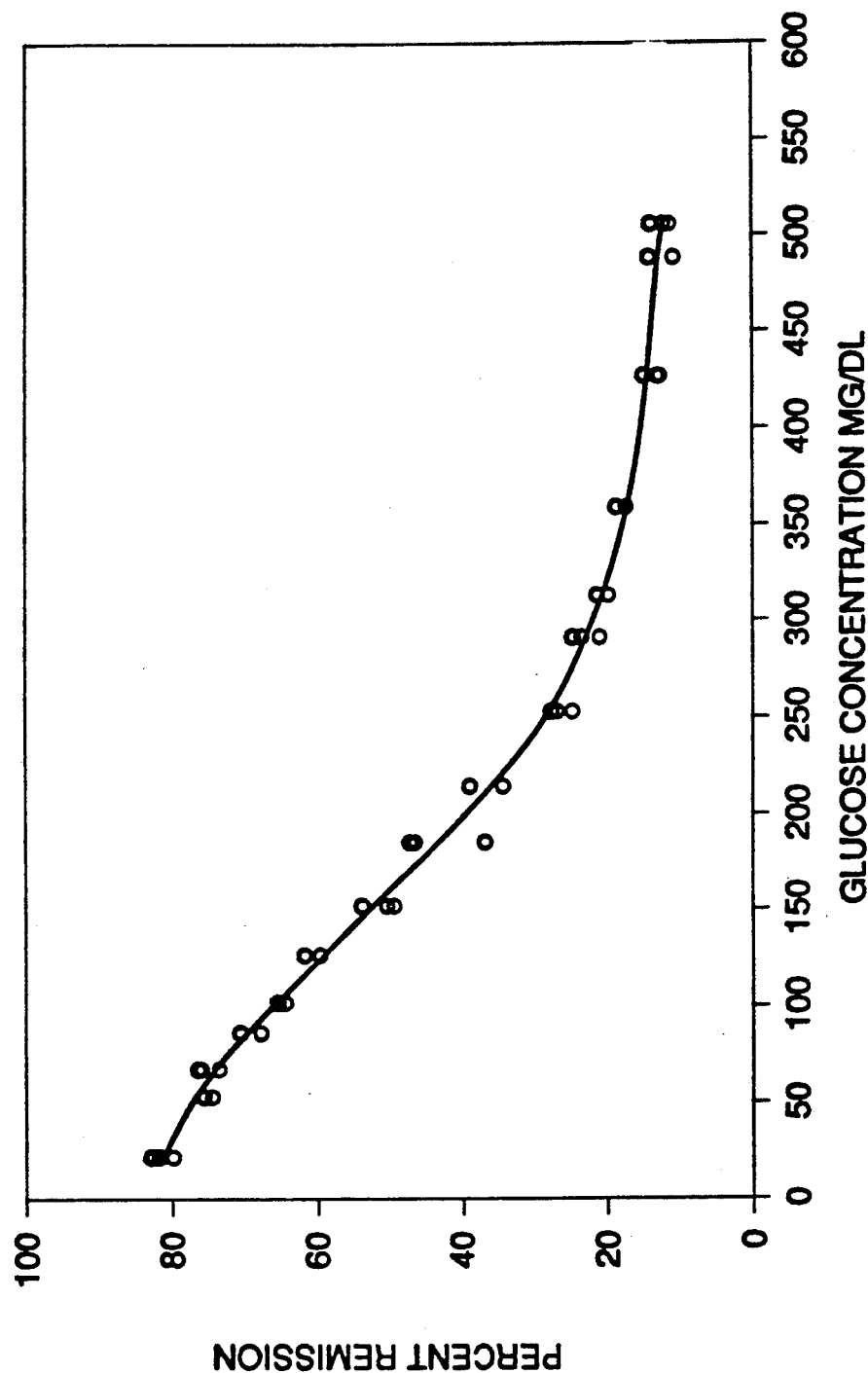
Figure 11:
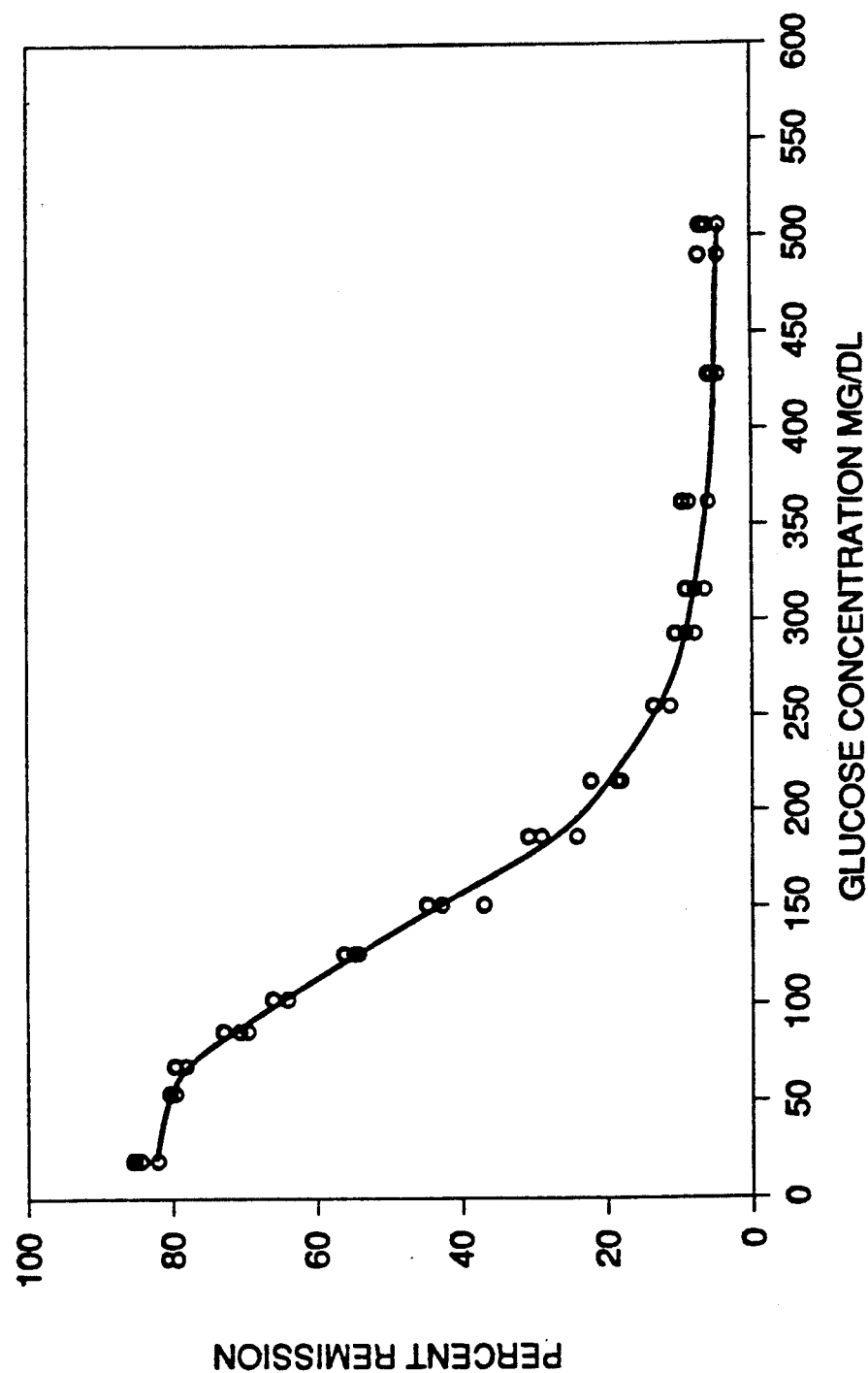

FIGS. 10 and 11, which present the results of these experiments show the desired smooth curve as the concentrations of glucose increase. Octyl gallate in particular shows an almost ideal figure—a line with almost uniform downward slope. This indicates that these compounds are also preferred in formulating the indicator compositions.

The foregoing examples 1-11 clearly show that controlled formation of detectable signal has been achieved via the inclusion of gallate derivatives in indicator compositions. While all of the gallate derivatives tested were operable, the preferred gallates are the propyl and octyl derivatives. All of these compounds, as well as the others, are depicted in FIG. 12.

One aspect of the invention will be seen to be compositions which are useful as indicators. These compositions contain indicator molecules which do not form coupled products (i.e., reducible chromogens) in the presence of the analyte which they are to detect, and a gallate derivative. It has been shown that the gallate derivative can be added directly to the indicator system without interfering with the operability of the molecule. The skilled artisan will note, however, that "one pot" reagents or compositions are not the only possible embodiment of the invention. Kits are envisioned, in which different components of the composition are presented in separate containers, which are then combined by the investigators prior to their use. For example, a typical kit includes a sample of a gallate derivative, such as the propyl or octyl ester, a non-coupling indicator system, such as 3,3',5,5'-tetramethylbenzidine and "APAC", each of which are in separate containers, and optionally contains enzymes such as GOD and POD, control solutions, and an analytical device, such as a test strip used to determine the analyte.

It will also be seen that the invention resides in analytical element, such as test strips, made up of a carrier, such as bibulous paper, which is impregnated or has incorporated therein the various indicator system components including the gallate derivative.

The examples also show that the invention teaches a method for determining an analyte containing sample contacts the indicator system and gallol derivative under conditions favoring generation of a detectable signal by the indicator system, followed by detection or determination of the signal. While glucose has been exemplified as the substance being determined, different analytes may also be determined. As is known to the skilled artisan, different materials such as various body fluids and exudates (blood, urine, semen, feces, pus tears, etc.), are frequently tested for various substances (pharmaceuticals and their by-products, illicit drugs, proteins, different carbohydrates, toxins, etc.), or the compounds described supra, such as bile acid derivatives; uric acid; cholesterol; HDLs and LDLs; components of blood; various enzymes, sarcosine and its derivatives such as creatine and creatinine; caffeine; and so forth. By choice or appropriate indicator systems, one can determine the particular antigen. Where non-coupling indicator systems are used, the gallol derivatives can be used to inhibit premature formation of the desired signal.

It will be understood that the specification and examples are illustrative but not limitative of the present invention and that other embodiments within the spirit and scope of the invention will suggest themselves to those skilled in the art.

We claim:

1. Composition useful in determining an analyte in a sample consisting essentially of (i) a non-coupling chromogen and (ii) a pyrogallol derivative or a pyrogallol ester.

2. Composition of claim 1, wherein said non-coupling chromogen is 3, 3', 5, 5' Tetramethylbenzidine.

3. Composition of claim 1, wherein said non-coupling chromogen is 3-amino-9- (gamma aminopropyl) carbazol.

4. Composition of claim 1, wherein said non-coupling chromogen is o-tolidine.

5. Composition of claim 1, wherein said pyrogallol derivative is gallic acid.

6. Composition of claim 1, wherein said pyrogallol derivative is methyl gallate.

7. Composition of claim 1, wherein said pyrogallol derivative is propyl gallate.

8. Composition of claim 1, wherein said pyrogallol derivative is octyl gallate.

9. Composition of claim 1, wherein said pyrogallol derivative is lauryl gallate.

10. Composition of claim 1, wherein said pyrogallol derivative is pyrogallol stearate.

11. Composition of claim 1, wherein said pyrogallol derivative is gallic acid N-butyl ester.

12. Composition of claim 1, wherein said pyrogallol derivative is gallic acid cetyl ester.

13. Composition of claim 1, wherein said pyrogallol derivative is gallic acid isobutyl ester.

14. Composition of claim 1, wherein said pyrogallol derivative is gallic acid isoamyl ester.

* * * * *